United States Patent
Skripitz et al.

[11] Patent Number: 5,116,377
[45] Date of Patent: May 26, 1992

[54] CEMENTABLE HIP PROSTHESIS

[75] Inventors: Walter Skripitz, Koblenz; Klaus-Dieter Schelhas, Bremen, both of Fed. Rep. of Germany

[73] Assignee: Bristol-Myers Squibb Company, New York, N.Y.

[21] Appl. No.: 507,148

[22] Filed: Apr. 10, 1990

[30] Foreign Application Priority Data

Apr. 15, 1989 [DE] Fed. Rep. of Germany ....... 3912465

[51] Int. Cl.$^5$ ................................................. A61F 2/32
[52] U.S. Cl. ..................................................... 623/23
[58] Field of Search ...................... 623/16, 18, 19, 20, 623/22, 23

[56] References Cited

U.S. PATENT DOCUMENTS 4,012,796 3/1977 Weisman et al. ..................... 623/23
4,698,063 10/1987 Link et al. .............................. 623/23

FOREIGN PATENT DOCUMENTS 1424829 9/1988 U.S.S.R. ................................ 623/23

Primary Examiner—David Isabella
Attorney, Agent, or Firm—Merchant, Gould, Smith, Edell, Welter & Schmidt

[57] ABSTRACT

A cementable thigh section of an acetabular prosthesis that has a shaft tapering toward its lower end, and on whose upper end is formed a flange-like support collar. Disposed in removable fashion below the support collar is an elastic spacer ring that at least partially covers the support collar. Worked in from the upper end of the thigh section is a boring that preferably branches out into branch borings, that comes out from the thigh section in the upper shaft portion, and serves for bringing the bone cement into the intermediate space between bone wall and thigh section after the thigh section is emplaced in the bone cavity.

17 Claims, 5 Drawing Sheets

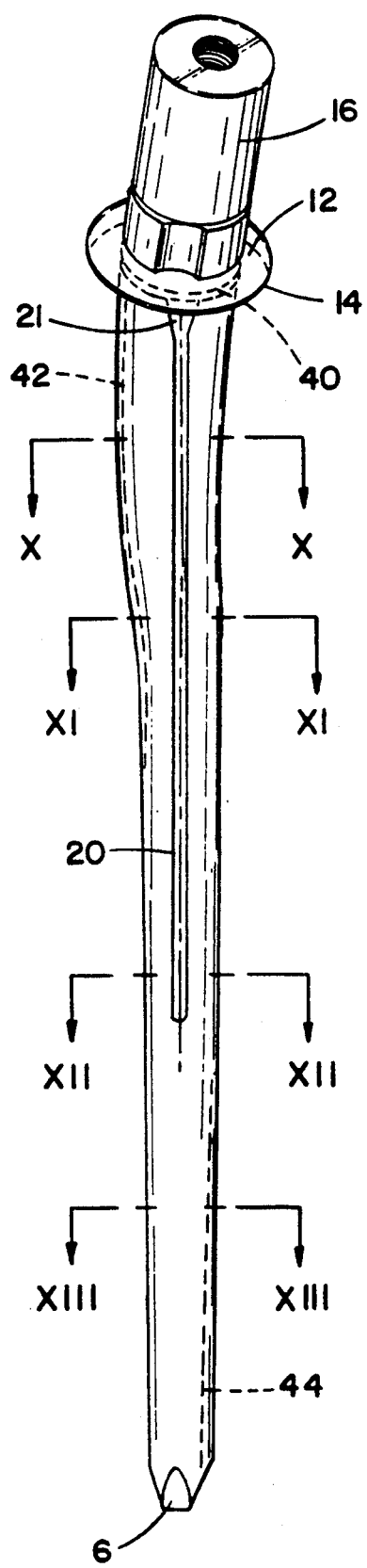
FIG. 2
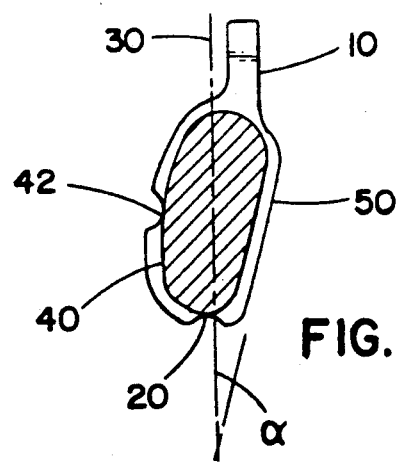
FIG. 3
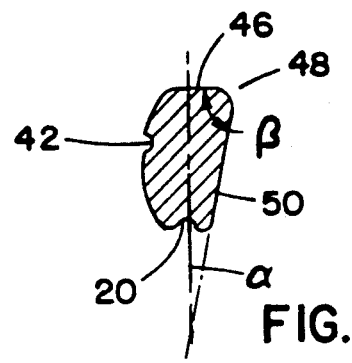
FIG. 4
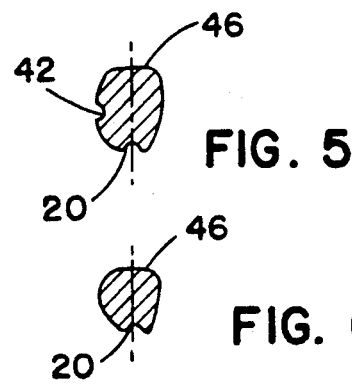
FIG. 5
FIG. 6
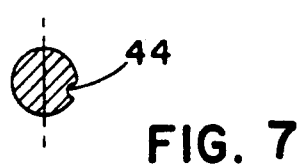
FIG. 7

CEMENTABLE HIP PROSTHESIS

The invention concerns a cementable thigh section of an acetabular prosthesis, with a aft that tapers toward the lower end, and with a flanged support collar on the shaft.

These types of thigh sections are known per se, for example from DE-OS 32 47 729, where the shaft is adapted, in the longitudinal direction, to the bone cavity of the natural thigh bone. Because of form-fitting to the natural bone cavity, the cross section of the shaft increases continuously toward the support collar and assumes under the support collar an oval, somewhat elliptical shape, whose longitudinal axis runs in a somewhat medial/lateral direction, while the transverse axis is aligned somewhat medially/dorsally. When implanting these types of thigh sections, the bone cavity, correspondingly prepared beforehand, is filled with bone cement, then the thigh section is pressed into the fresh bone cement. To obtain a firm prosthesis/bone joint that is stable and loosening-free over a long period of utilization, the shaft should here be surrounded over its entire length and the entire periphery with an adequately thick, relatively homogeneous layer of cement in order, on the one side, to anchor the shaft in form-locking fashion in the cement and, on the other side, to anchor the cement in form-locking fashion in the adjoining bone tissue. However, it has been demonstrated in practice that when placing the thigh section into the cement bed, the fresh cement in the proximal portion of the shaft that is underneath the support collar is substantially displaced, particularly in the medial region, such that formed in this region is only a thin cement layer, or none at all. If, however, the layer of cement in this region that is essential for the introduction of force is too thin, then capable of occurring from the continuous, essentially periodic loading of the thigh section because of the walking movement, is a stronger relative movement between thigh section and bone and, therewith, also a relative movement between shaft and cement jacket, whereby parts of the thin cement layer break and, in this manner, can cause a loosening of the entire thigh section. Additionally, with these types of known thigh parts, there exists the danger that an insufficient, nonhomogeneous or even partially interrupted cement layer will be formed between the resection edges of the natural patient femur and the support collar, so that a direct contact between bone and the support collar, along with the therewith associated unfavorable effects, can not be positively avoided.

Therefore, the object of the invention is to further develop the cementable thigh section of the initially-mentioned type such that there is also realized in the medial region an adequate anchoring of the shaft, and that a thorough, uniform layer of cement will be realized between support collar and patient femur.

This objective is met in accordance with the invention in the case of the thigh section of the initially-mentioned type by means of a separable elastic spacer ring running about the shaft on the underside of the support collar, and a boring running from the top through the support collar that comes out from the thigh section in the upper shaft portion.

Alternatively, this objective is met in accordance with the invention in the case of the thigh section of the initially-mentioned type by means of a separable elastic spacer ring running about the shaft that lies against the underside of the support collar, and a boring running through the support collar from above, which, in the upper-shaft portion, branches out into several branch borings coming out from the shaft.

The advantages of the invention lie particularly in the fact that the elastic spacer ring, when installing the thigh section, enables a centering relative to the wall of the patient femur, and that next the entire and/or the still lacking portion of the bone cement will be pressed in through the boring and possibly the branch borings, between the thigh section and the patient femur. Because of the initial fixing of the thigh section by means of the spacer ring, the intermediate space between the thigh section and the bone wall can be established in defined fashion, and the bone cement pressed in later into this intermediate space fills this intermediate space without, in so doing, the thigh section shifting inside the bone cavity and thereby generating nonhomogeneous layers of cement. After pressing in a sufficient amount of bone cement, the spacer ring, for example on an appropriate butt strap, is pulled away from the thigh section so that now—with further pressing in of bone cement—the open space from the spacer ring that is produced is also filled with bone cement, so that direct contact between the metallic support collar and the patient femur is reliably prevented by a homogeneously-thick layer of cement. If necessary, the thigh section can finally still be driven in slightly further in the axial direction in order to assure the homogeneous filling of all intermediate spaces with bone cement and a good seating of the thigh section.

Particularly preferred, the branch borings, into which the main boring branches, have a reduced diameter relative to the main boring. The branch borings come out of the shaft in distributed fashion at the periphery. Particularly preferred, one branch boring leaves the shaft laterally and another branch boring leaves the shaft medially, so that the fluid bone cement can more easily be distributed homogeneously about the shaft of the prosthesis.

Particularly preferred, formed in the shaft below the support collar is a circular circumferential groove in which the spacer ring is journaled. Then, when the spacer ring is removed or cut off, the bone cement—with further post-pressing—can also fill the circumferential groove, whereby direct contact between the metal support collar and the patient bone is still better prevented.

In accordance with a particularly preferred form of embodiment of the invention, the shaft has medially a longitudinal groove that opens out into the circumferential groove. When the bone cement, as it is pressed in, reaches the medial longitudinal groove, the bone cement forms in this longitudinal groove a ribbed thickening of the cement jacket. This cement rib forms a solid, form-locking anchoring flange that protects the prosthesis, in particular against rotational stressing or torsional stressing about the shaft axis.

Additionally, the still-flowable cement is distributed uniformly in the direction of the shaft through the medial longitudinal groove, excess cement being capable of flowing off, particularly toward the support collar into the circumferential groove.

It there is a conical pin on the support collar for attaching a prosthesis head, the boring preferentially runs centrally through this pin and, in particularly preferred manner, leaves the upper shaft portion rectinlinearly in extension of the shaft axis. Realized in this manner is an adequate cross section for pressing the cement through without that the carrying cross section of the thigh section be too strongly weakened thereby. Further, the pressed-in cement enters sufficiently deeply into the bone cavity to be able to run uniformly toward the shaft end and finally toward the support collar. In the case of thigh sections with a lateral, nose-shaped stube at the upper shaft end, the boring can alternatively also pass through this stub—approximately parallel to the pin axis.

According to a particularly preferred form of embodiment of the invention, the spacer ring consists of an elastic sealing material and displays in the plane below the collar an expansion such that is lies, over its entire circumference, with its underside on the resection edge of the patient femur. The spacer ring preferably includes one or several spacing elements that establish the desired interval between the shaft and the bone wall, with this interval capable of being a function of the circumferential angle or—alternatively —also be constant along the entire circumference. With this form of embodiment of the invention, when emplacing the thigh section, the bone cavity, appropriately prepared beforehand, can be sealed in sufficiently airtight fashion by the spacer ring lying against the resection edge, and can then be acted upon by a vacuum, before and during pressing in of the cement, through a suction opening made through the bone wall, whereby the cement is drawn in and distributed rather rapidly and uniformly into the intermediate space between the thigh section and bone. After removing the sealing ring, for final positioning the thigh section must still be driven in slightly, mechanically, deeper into the bone cavity, whereby the post-flowing cement fills the circumferential groove and the intermediate space between support collar and bone.

The spacer ring preferably has a parting line or a specified separation place and a pull strap for pulling away the spacer ring, so that the spacing element can be removed easily from the thigh section manually.

To improve distribution of the bone cement during the pressing-in process, and additionally in order to improve resistance to rotation and anchoring to the bone, it is possible to form in the upper and/or in the lower shaft region additional longitudinal grooves in the shaft.

Explained in more detail in the following with the aid of the drawing will be an example of embodiment of the invention.

FIG. 2 shows a front view of the thigh section of FIG. 1 in the direction of the arrow II;

FIGS. 3 to 7 show cross sections along the lines III-—III to VII-VII of FIG. 2;

Figure 1:
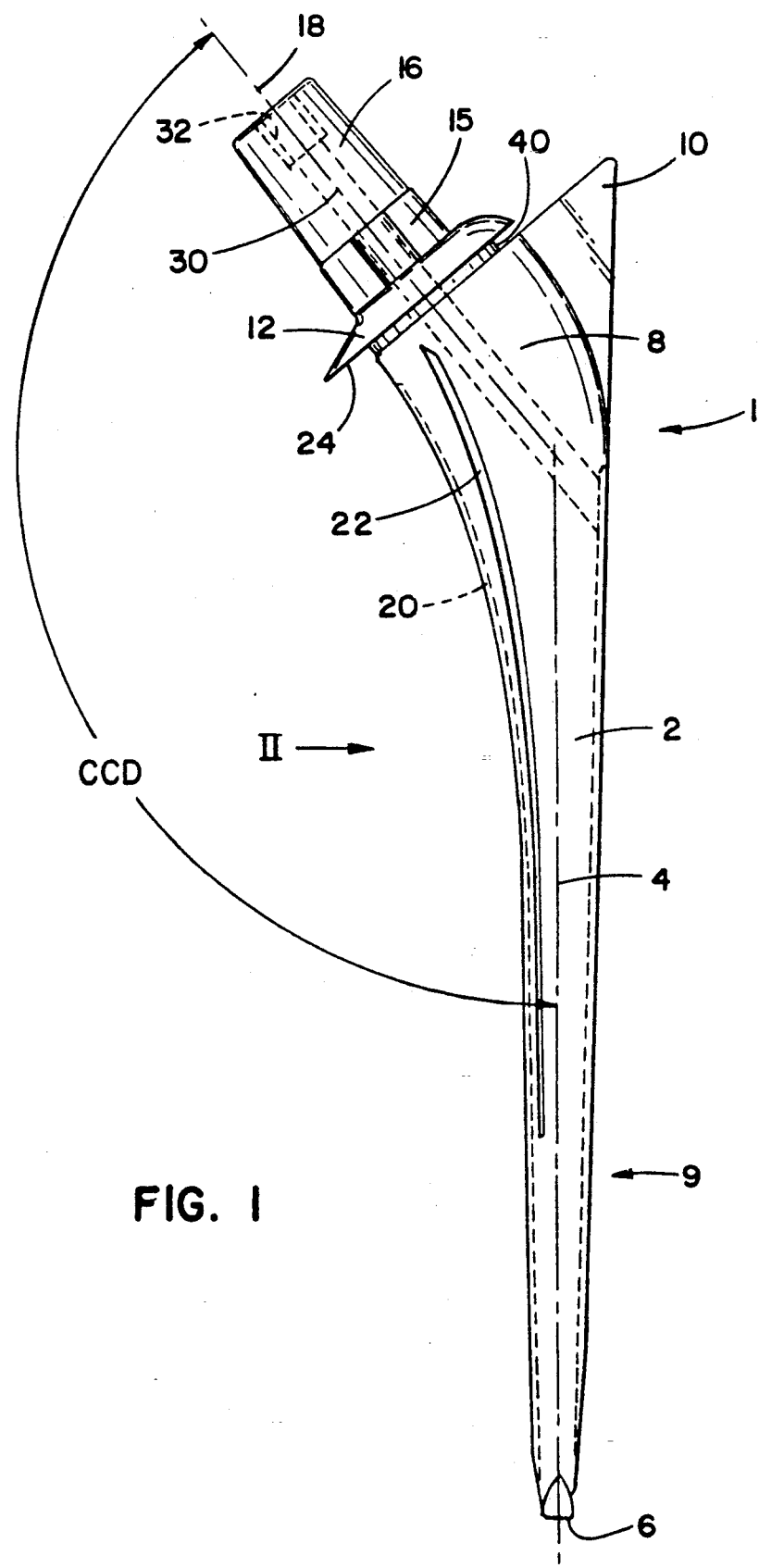
FIG. 1 shows a side view of the thigh section.
Figure 8:
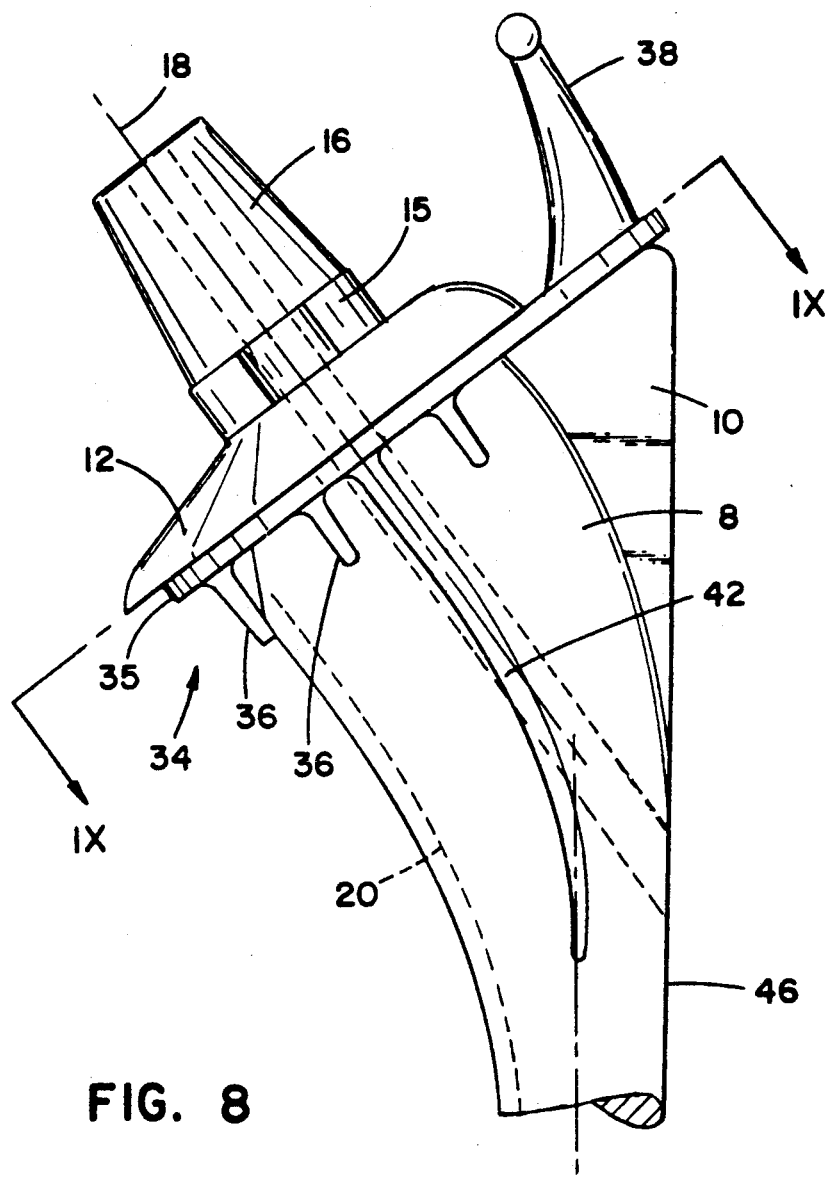
FIG. 8 shows an enlarged representation of the upper shaft region of the thigh section in accordance with FIG. 1.
Figure 9:
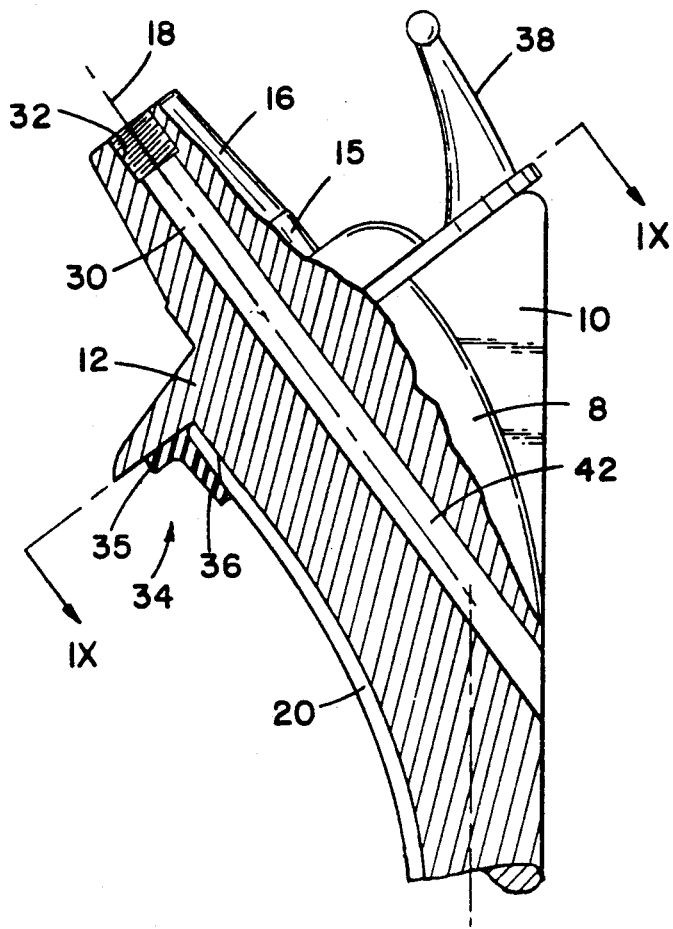
FIG. 9 shows a representation corresponding to FIG. 8 in a cut.

FIG. 1 and 2 show a cementable thigh section of an acetabular prosthesis dorsally, respectively medially. FIG. 8 and 9 show a partial view, corresponding to FIG. 1, of the top end of the thigh section in an enlarged representation, partially in a cut. FIG. 3 to 7 represent cross sections through the shaft 2 of the thigh section at different levels. The thigh section 1 has a shaft 2 that tapers constantly toward its lower end 6, with the cross section of the shaft in each case being adapted approximately to the bone cavity of the natural femur. The shaft carries at its upper, so-called proximal end 8 a support collar 12 that overhangs the shaft 2. Disposed on the support collar 12 is a polygonal portion 15 that passes over into a conical pin 16 for acceptance of a prosthetic hip head. The cone portion 16, the polygonal portion 15 and the upper end portion 8 of the shaft 2 have a common axis 18 that includes an angle CCD to the shaft axis 4 of, for example, 125° to 160°. Instead of the single-piece construction of shaft 6, support collar 12 and conical pin 16 represented here, it is alternatively also possible to provide the shaft 2 only with a support collar 12 and a conical internal boring running along the axis 18, and to construct the conical pin 16 as a separate part which—in the direction of the axis 18 contains an additional anchoring cone that can be plugged into the conical internal boring for anchoring the shaft 2. Alternatively, also possible is the construction of the thigh section with a single-piece, formed-on prosthetic hip head.

The cross section of the shaft 2—as a function of the distance from its lower end 6—is in each case adapted to the cross section of the bone cavity of the natural femur bone. In the lower region 9 of the shaft 2 it has almost the form of a circle and passes over into an oval cross section toward the support collar. Formed below the support collar 12, laterally on the shaft 2, is a stub 10 that runs laterally outwardly and displays a transversely-running extraction boring 10a.

In its medial region, the shaft 2 has a longitudinal groove 20 that extends in the top shaft portion 8 from the support collar 12, downwardly out to over the center of the shaft 2 and runs out in the lower shaft portion 9. Formed dorsally in the top shaft portion 8 is another longitudinal groove 42 that runs below the support collar 12, approximately in the direction of the axis 18 of the pin 16 and —following the curvature of the shaft- —finally runs out again, in the direction of the shaft axis 4, in the top shaft portion 8. Formed ventrally in the lower shaft portion 9 is a longitudinal groove 44 that ends below the middle of the shaft; compare FIG. 2 and 7. The longitudinal grooves 20, 42 and 44, when implanting the thigh section, accommodate in defined fashion bone cement in an amount that suffices for assuring a positive, form-locking anchoring of the bone cement in the adjoining bone tissue and—after setting —forming in the longitudinal grooves 20, 42, 44 cement ribs that prevent a rotation of the thigh section 1 over the entire shaft length, and therewith prevent loosening.

The medial longitudinal groove 20 and also the dorsal longitudinal groove 42 widen below the support collar 12 and open out into a circumferential groove 40 that is formed in the shaft 2, below the support collar 12, and possibly yet to a predetermined depth into the support collar 12, and additionally serves so that when implanting the thigh section cement flows in the longitudinal grooves 20, 42 against the support collar 12 and is distributed there on the underside of the support collar 12 in a cohesive layer to prevent an undesired, direct contact between the thigh section and the femur bone in the region of the resection edge of the bone also. If desired, the circumferential groove 40 can be in communication with a radial groove on the underside of the support collar 12 in order that excess cement be able to run outwardly during the implantation.

As can be obtained in particular from the cross sections in accordance with FIG. 3 to 7, formed laterally on the shaft 2, in the upper shaft portion 8, is a flat contact surface 46 that runs approximately perpendicularly to the medial/lateral plane 30 and finally passes over into the nose-shaped stub 10 which, in the example of embodiment illustrated, is offset sidewardly against the medial/lateral plane 30. To be able to anchor the shaft 2 laterally in the patient bone, needing to be worked in when implanting is a corresponding recess in the bone which, in the lateral region of the prosthesis, approximately represents a form-fitting between prosthesis and bone. The upper shaft portion 8 is furthermore constructed such that its ventral cross section is approximately limited my a straight line 50 that cuts the medial/lateral plane at an angle $\beta$, with the angle $\beta$ changing over the length of the shaft. The contact surface 46 and the ventral surface portion defined by said straight line 50 here forms—over a predetermined shaft length—a rounded edge 48 that includes the angle $\beta$ and, with corresponding out of the bone bed, forms a particularly effective protection against rotation and torsion.

Figure 10:
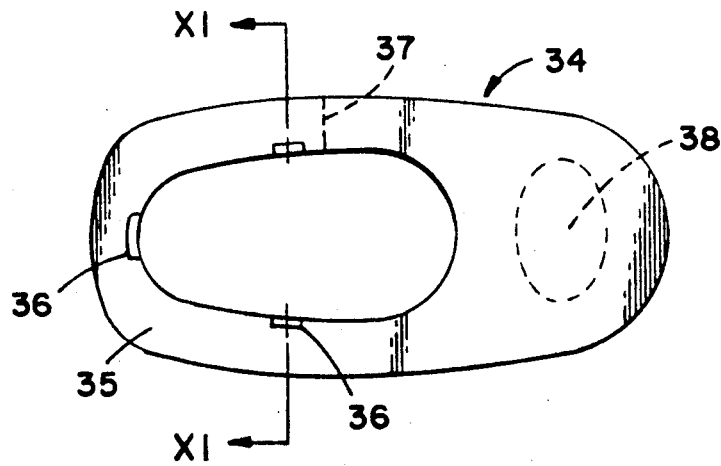
FIG. 10 shows a top view onto the spacer ring.

As can be obtained in particular from FIG. 1 and 9, the thigh section 1 has a spacer ring 34 made of elastic material, which is disposed in the circumferential groove and that covers the support collar 12, at least partially, and the stub 10 in completely flat fashion, and overhangs substantially laterally, and during implantation of the thigh section can be removed at a suitable point in time. Additionally to the floor surface 35, which covers the undersurface of the support collar 12 and covers over the stub 10, the spacer ring 34 has a spacing element 36 running perpendicularly hereto, therefore running against the shaft in the direction of the axis 18, said spacing element defining a predetermined distance to the surface of the shaft 2. The thickness of the spacing element 36 can here be constant over the entire spacer ring 34 or, alternatively, vary along the circumference in desired fashion. As can be obtained in particular from FIG. 10, the spacer ring 34 has a parting line 37 that allows a simple removal of the spacer ring 34, e.g. by a pull on a pull strap 38, because the parting line breaks under the pulling action.

The spacer ring 34 extends outwardly in the plane below the support collar 12, over its entire circumference, up to or past the resection area of the patient femur, in order to obtain good sealing of the bone cavity. Additionally, the support collar 12 can extends to past the lateral stub 10, the spacer ring then running below the support collar 12, also about the stub 10, and when installing the prosthesis it will be pushed by the support collar 12, over its entire circumference, against the resection area of the patient femur.

The thickness of the spacing element 36 is—possibly by additionally-formed bulges or flanges—dimensioned such that the spacing element 36, when emplacing the thigh section into the patient femur, fills the intermediate space between the thigh section and the hard bone wall of the patient femur, and thereby positions the thigh section in the patient femur such that the thigh section is surrounded below the support collar 12, over its entire circumference, by an open space of desired thickness for accepting bone cement.

As can be obtained in particular from FIG. 1, 8 and 9, worked in from the top end of the thigh section 1 is a boring 30 that extends centrally through the conical pin 16 and runs in extension of the pin axis 18, and comes out from the thigh section 1 in the shaft portion 8. The boring 30 serves for spraying in the bone cement after placing the thigh section 1 into the bone cavity. To simplify attachment of the spraying nozzle to the cement sprayer, the boring 30 can include an internal thread 32 or the like for the removable attachment of the spraying nozzle. The cross section of the boring 30 must be large enough so that the bone cement can be pressed into the intermediate space between bone wall and thigh section. On the other hand, a too-large diameter for the boring 30 should be avoided in order to guarantee a sufficient mechanical stability of the thigh section.

Figure 11:
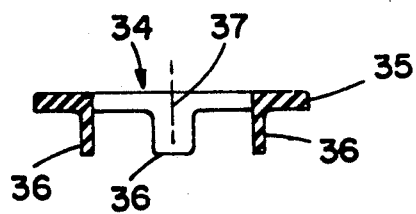
FIG. 11 shows a cross section through the spacer ring along the line XI—XI of FIG. 10.
Figure 12:
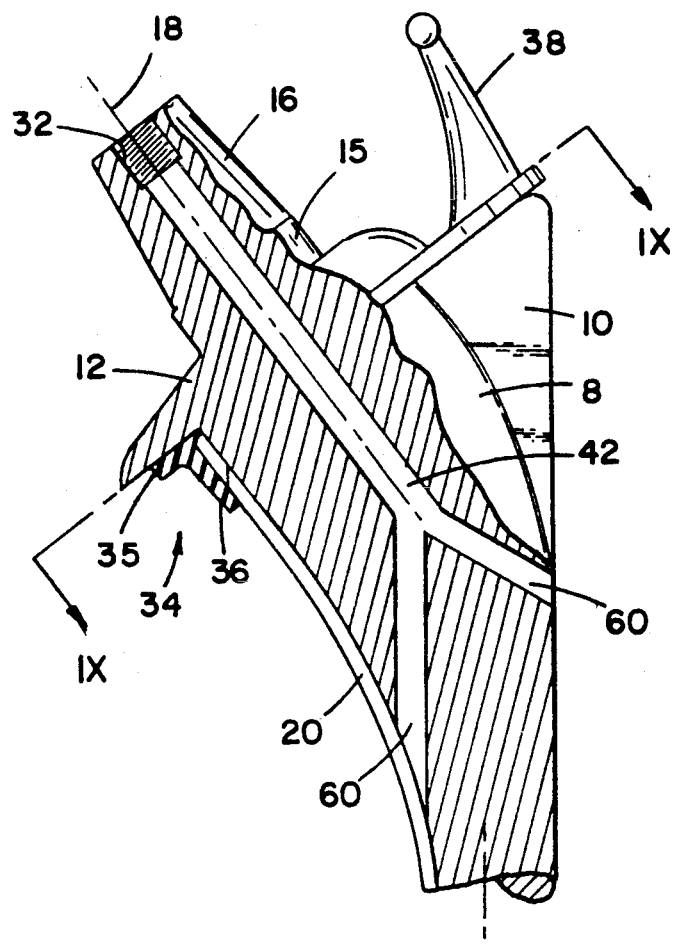
FIG. 12 shows another example of embodiment of the prosthesis in a representation corresponding to FIG. 9

FIG. 12 shows another form of embodiment of the thigh section of an acetabular prosthesis that corresponds substantially to that in accordance with FIG. 9. However, while in the case of the prosthesis in accordance with FIG. 9 the boring 30 penetrates, with a constant cross section, through the pin 16, the support collar 12 and the upper shaft portion, the boring 30 in the form of embodiment in accordance with FIG. 11 is guided up into the upper shaft portion 8 and then branches there into two partial borings 60. A partial boring 60 is guided out laterally from the shaft 2 with a reduced cross section, the other partial boring 60 extends, also with reduced cross section, medially and comes out from the shaft 2 in the medial longitudinal groove 20. Additionally, still other branch borings 60 can also be arranged in distributed fashion on the circumference and possibly come out of the shaft 2 offset in height, in order to distribute the cement more uniformly about the shaft when pressing it in.

Implantation of the thigh section 1 is done in the following manner: after preparation of the bone cavity, the thigh section, together with the spacer ring 34, is placed into the bone cavity, so that the spacing element 36 of the spacer ring 34 comes to lie between bone wall and thigh section, and establishes the position of the thigh section in the bone cavity. Additionally, the support collar 12 presses the floor area 35 of the spacer ring 34 firmly against the resection edge of the bone, so that the defined hollow space of the spacing element 36 is sealed upwardly between bone wall and thigh section.

Next, the bone cement is pressed in through the boring 30 into the intermediate space between thigh section 1 and bone wall. Assured by sufficient pressure is that the bone cement will distribute itself uniformly in this intermediate space and thereby form a relatively homogeneous intermediate layer between bone wall and thigh section. The longitudinal grooves 20, 42 and 44 here serve for distributing the bone cement in the longitudinal direction of the shaft 2. If the intermediate space between thigh section 1 and the bone wall is filled with bone cement, the spacer ring is next removed from the prosthesis and more cement is pressed in, so that sufficient bone cement reaches into the space below the support collar that has been filled beforehand from the spacer ring, and thereby prevents a direct contact between support collar and bone. If desired, another boring can also be made at a suitable place through the bone wall from the outside into the prepared bone cavity, and the bone cavity can be placed under a vacuum through this boring by means of a suction pump while pressing in the bone cement, whereby introduction of the bone cement is considerably improved and accelerated.

We claim:

1. An implantable femoral prosthesis for cementation in a prepared intramedullary canal of a femur, said prosthesis comprising:

an elongated shaft tapering from a proximal end to a distal end, said proximal end having a support collar formed thereon, said collar extending radially outwardly from said shaft and being configured to engage a resected surface of the femur, and said shaft including a circumferential groove formed therein adjacent and below said collar, and a longitudinal groove formed in a medial surface of the shaft and opening into said circumferential groove; and a separable elastic spacer ring configured to be disposed on said support collar and at least partially in the circumferential groove; and a main bore extending from the proximal end of the shaft, above the collar through the support collar downwardly into a trochanter region of the shaft and outwardly of a surface in a thigh region of the shaft.

2. An implantable femoral prosthesis according to claim 1, characterized by the fact that the main bore runs centrally through a conical pin formed on the support collar.

3. An implantable femoral prosthesis according to claim 2 wherein said bore rune through an upper portion of said shaft about an axis of the conical pin.

4. An implantable femoral prosthesis according to claim 1, characterized by the fact that formed laterally at an upper portion of the shaft is a nose-shaped stub through which the main bore runs, and that the spacer ring extends past the stub.

5. An implantable femoral prosthesis according to claim 1, characterized by the fact that the spacer ring comprises an elastic sealing material.

6. An implantable femoral prosthesis according to claim 1, characterized by the fact that the spacer ring contains at least one spacing element that establishes a predetermined distance from the femur to the surface of the shaft.

7. An implantable femoral prosthesis according to claim 6, characterized by the fact that the spacing elements respectively establish along the circumference of the shaft a different distance from the femur to the surface of the shaft.

8. An implantable femoral prosthesis according to claim 6, characterized by the fact that each spacing element is formed as a circular stub on the spacer ring, each spacing element lying against the surface of the shaft.

9. An implantable femoral prosthesis according to claim 6, characterized by the fact that formed as spacing elements on the spacer ring, are several stubs lying against the surface of the shaft and running in the direction of the shaft.

10. An implantable femoral prosthesis according to claim 1, characterized by the fact that the spacer ring has a parting means at a specified place of separation and a strap, said parting means and strap adapted for pulling off the spacer ring.

11. An implantable femoral prosthesis according to claim 1, characterized by the fact that there is formed dorsally in an upper portion of said shaft a longitudinal groove opening out into the circumferential groove.

12. An implantable femoral prosthesis according to claim 1, characterized by the fact that there is formed ventrally in a lower shaft portion a longitudinal groove.

13. An implantable femoral prosthesis for cementation in a prepared intramedullary canal of a femur, said prosthesis comprising:

an elongated shaft tapering from a proximal end to a distal end, said proximal end having a split support collar formed thereon, said collar extending radially outwardly from said shaft and being configured to engage a resected surface of the femur, and said shaft including a circumferential groove formed therein adjacent and below said collar, and a longitudinal groove formed in a medial surface of the shaft and opening into said circumferential groove; and a separable elastic spacer ring configured to be disposed on said support collar and at least partially in the circumferential groove; and a main bore extending from the proximal end of the shaft, above the collar through the support collar downwardly into a trochanter region of the shaft and then branches out into a plurality of branch bores that exit the shaft.

14. An implantable femoral prosthesis according to claim 13, characterized by the fact that the branch bores have a reduced cross sectional area relative to the main bore cross sectional area.

15. An implantable femoral prosthesis according to claim 13, characterized by the fact the branch bores come out from the shaft, and are distributed circumferentially about the shaft.

16. An implantable femoral prosthesis according to claim 13, characterized by the fact that a first of the branch bores comes out laterally, and a second of the branch bores comes out medially from the shaft.

17. An implantable femoral according to claim 10, wherein said parting means comprises a parting line formed in the spacer ring.

* * * * *

UNITED STATES PATENT AND TRADEMARK OFFICE
CERTIFICATE OF CORRECTION

PATENT NO. : 5,116,377
DATED : May 26, 1992
INVENTOR(S) : Walter Skripitz et al

It is certified that error appears in the above-indentified patent and that said Letters Patent is hereby corrected as shown below:

In column 1, line 5, delete "aft" and insert --shaft-- therefor.

In column 2, line 64, "IT" should be "if".

In column 2, lines 67, 68, delete "rectinlinearly" and insert --rectilinearly-- therefor.

In column 3, line 14, delete "is" and insert --it-- therefor.

In column 3, line 47, after "shaft" insert --Advantageous further development of the invention are characterized by the features of the subclaims.--

In column 7, line 30, delete "rune" and insert --runs-- therefor.

In column 8, line 44, after "fact" insert --that--.

UNITED STATES PATENT AND TRADEMARK OFFICE
CERTIFICATE OF CORRECTION

PATENT NO. : 5,116,377

DATED : May 26, 1992

INVENTOR(S) : Walter Skripitz et al

It is certified that error appears in the above-indentified patent and that said Letters Patent is hereby corrected as shown below:

In column 8, line 51, after "femoral" insert --prosthesis--.

Signed and Sealed this

Seventh Day of December, 1993

Attest:

BRUCE LEHMAN

*Attesting Officer*   *Commissioner of Patents and Trademarks*